Figure 1:
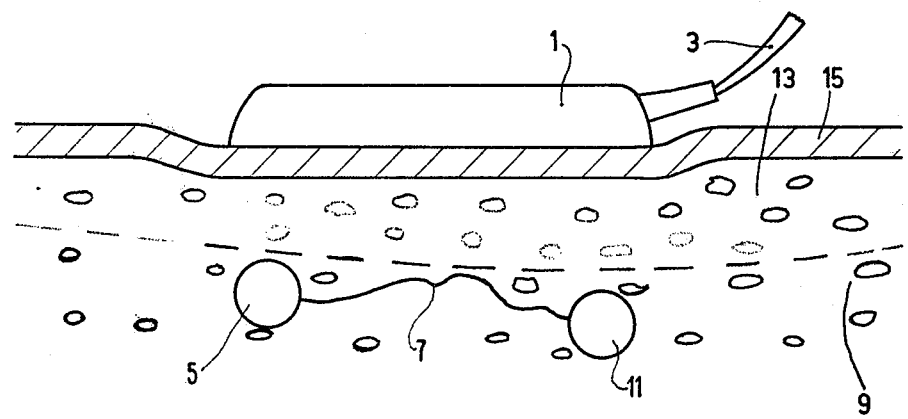

United States Patent [19]

Kimmich

[11] 4,252,123
[45] Feb. 24, 1981

[54] DEVICE FOR THE TRANSCUTANEOUS ELECTROCHEMICAL DETERMINATION OF THE PARTIAL OXYGEN PRESSURE IN BLOOD

[75] Inventor: Hans-Peter Kimmich, Nijmegen, Netherlands

[73] Assignee: U.S. Philips Corporation, New York, N.Y.

[21] Appl. No.: 10,768

[22] Filed: Feb. 9, 1979

[30] Foreign Application Priority Data

Feb. 20, 1978 [NL] Netherlands ..................... 7801869

[51] Int. Cl.$^3$ .............................................. A61B 5/00
[52] U.S. Cl. ................................ 128/635; 204/195 B
[58] Field of Search ............................. 128/632, 635; 204/195 B

[56] References Cited

U.S. PATENT DOCUMENTS

| | | | |
|---|---|---|---|
| 3,795,239 | 3/1974 | Eberhard et al. | 128/635 |
| 3,985,633 | 10/1976 | Lubbers et al. | 128/635 |
| 4,114,602 | 9/1978 | Huch et al. | 128/635 |

OTHER PUBLICATIONS

Butler, J. et al., "A Multicathode Oxygen Sensor Fabricated Using Integrated Circuit Techniques", Conf: 5th Canadian Med. & Biol. Engrg. Conf., Montreal, Quebec, Canada, 3–6 Sep., 1974, pp. 5.2a, b.

Brown, E. G. et al., "A Unique Electrode Catheter for Continuous Monitoring of Arterial Blood Oxygen Tension in Newborn Infants", in *Oxygen Transport To Tissue*, Plenum Publs., N. Y., 1973.

Primary Examiner—Robert W. Michell
Assistant Examiner—Francis J. Jaworski
Attorney, Agent, or Firm—Thomas A. Briody; Robert T. Mayer; Jack E. Haken

[57] ABSTRACT

A device for the transcutaneous electrochemical determination of the partial oxygen pressure in blood, comprising a measuring head which includes at least three measuring cells of the Clark-type, comprising periodically actuated heating elements, the actuation of the heating elements being realized at a phase difference such that always at least one measuring cell provides a reliable measuring value.

2 Claims, 8 Drawing Figures

DEVICE FOR THE TRANSCUTANEOUS ELECTROCHEMICAL DETERMINATION OF THE PARTIAL OXYGEN PRESSURE IN BLOOD

The invention relates to a device for the transcutaneous electrochemical determination of the partial pressure of oxygen in the blood of humans or animals, comprising a measuring head which includes a measuring cell which is provided with electrodes and which comprises a surface which is to be arranged in contact with the skin and which can be heated by an electrical heating element.

A device of this kind is known from Netherlands Patent Specification No. 152,084. The measuring cell comprises a measuring electrode which is made of, for example, platinum and a reference electrode which is made of, for example, silver/silver chloride. These electrodes are arranged in an electrolyte, for example, A KCl solution which is separated from the surroundings by an oxygen-permeable diaphragm. A measuring cell of this kind is known as a Clark cell. In the known device, the Clark cell furthermore comprises a heating element whereby the surface thereof which is to be arranged in contact with the skin can be heated. This heating element on the one hand serves to widen the peripheral blood vessels, so that the supply of blood is increased and the peripheral venous system is actually filled with arterial blood at this area, while on the other hand it serves to accelerate the oxygen diffusion through the skin. Experiments have demonstrated that a better correlation between the arterial partial oxygen pressure and the transcutaneously measured oxygen pressure is thus obtained. A more thorough consideration of the various factors on which the transcutaneously measured oxygen pressure depends, however, shows that this correlation is good only if these factors cancel each other more or less by chance.

In arterial blood an equilibrium exists between the percentage of oxidized haemo-globin and the partial oxygen pressure. When the blood is heated, this equilibrium is shifted so that the partial oxygen pressure increases. Therefore, when the described measuring method is used, the partial oxygen pressure in the peripheral blood vessels is higher than in the arteries. During the diffusion through the skin, the skin cells consume oxygen, so that the oxygen pressure at the area of the epidermis is lower than in the peripheral blood vessels. Finally, the measuring cell also consumes a given quantity of oxygen. If all these influences just cancel each other, the partial oxygen pressure measured equals the arterial oxygen pressure.

It has been found that this correlation is still poor at a skin temperature of 43° C. and often good at 44° C. A higher temperature causes pain and burning of the skin. Irritation can also occur at 44° C., if the duration of the measurement is a few hours or more. Therefore, it is customary to move the measuring head to another area of the skin after every two hours, which implies additional work for the physician or the nurse and which, moreover, increases the risk of errors.

The invention has for its object to provide a device of the described kind which can be used in one position for a very long period of time without objection and which, moreover, enables the separate determination of the effect of at least a number of the factors which influence the correlation between the measured oxygen pressure and the actual arterial oxygen pressure.

To this end, the device in accordance with the invention is characterized in that the measuring head comprises at least three measuring cells, each cell having its own heating element, the electrodes of each measuring cell forming part of a separate measuring circuit, the heating elements being connected to a power supply circuit which is adapted for the periodical actuation of the heating elements for $T_1$ minutes, there being an interval of $T_2$ minutes between two actuations, $T_1$ and $T_2$ being the same for all heating elements and the actuation of a heating element commencing at an instant which lies $(T_1+T_2)/n$ minutes after the beginning of the actuation of the preceding heating element, n being the number of heating elements.

A preferred embodiment of the device in accordance with the invention is characterized in that the measuring cells are mounted in a body having a low heat conductivity, the surface of the measuring cells which can be heated being situated in substantially the same plane as a surface of the body, said surface being surrounded by a non-heated surface of an annular measuring cell which is situated in the same plane and which is to be arranged against the skin, said measuring cell being accommodated in a housing together with said body.

The invention will be described in detail hereinafter with reference to the accompanying diagrammatic drawings.

Figure 2:
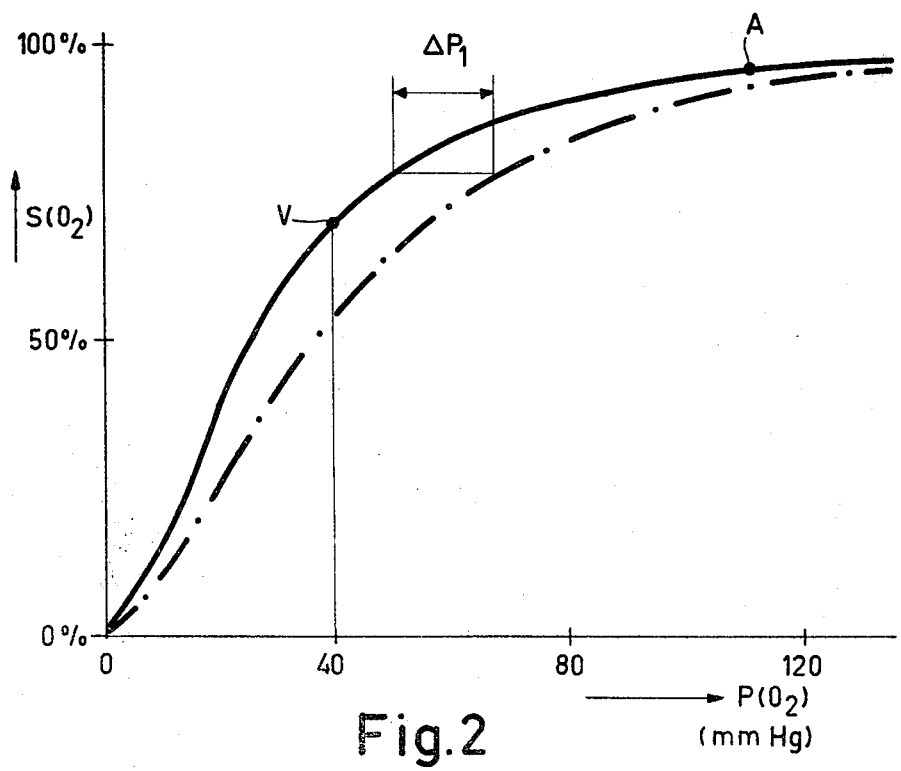
Figure 3:
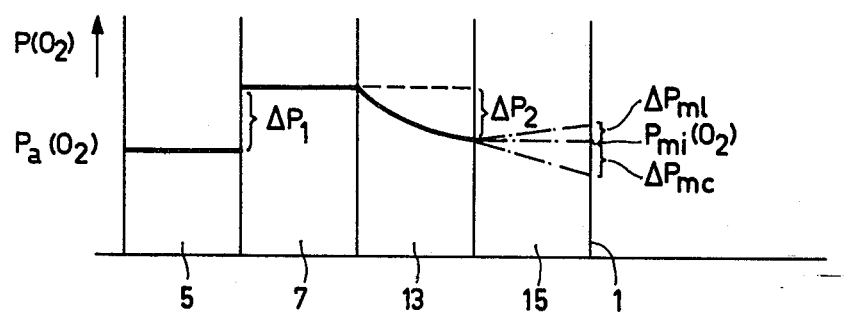
Figure 4:
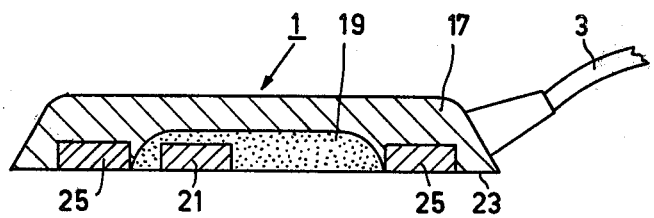
Figure 5:
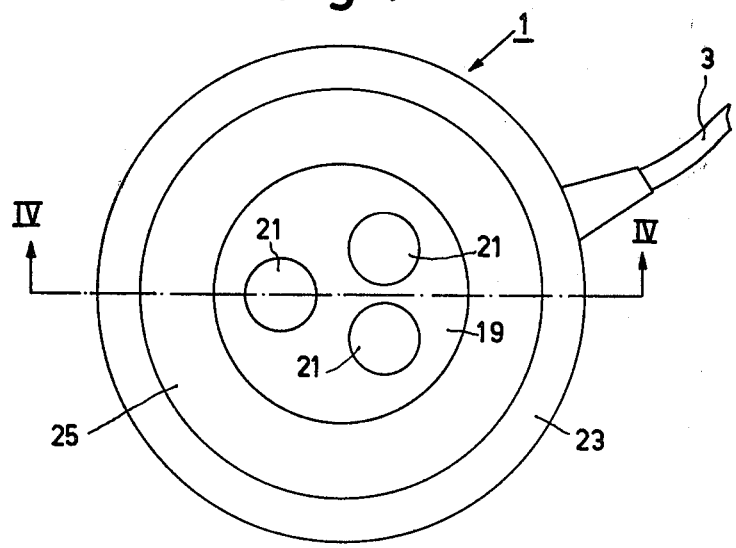
Figure 6:
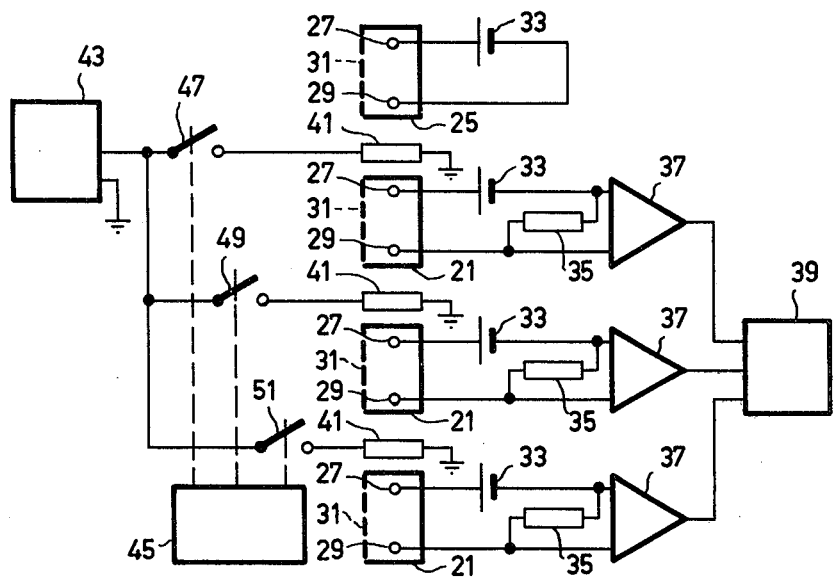
Figure 7:
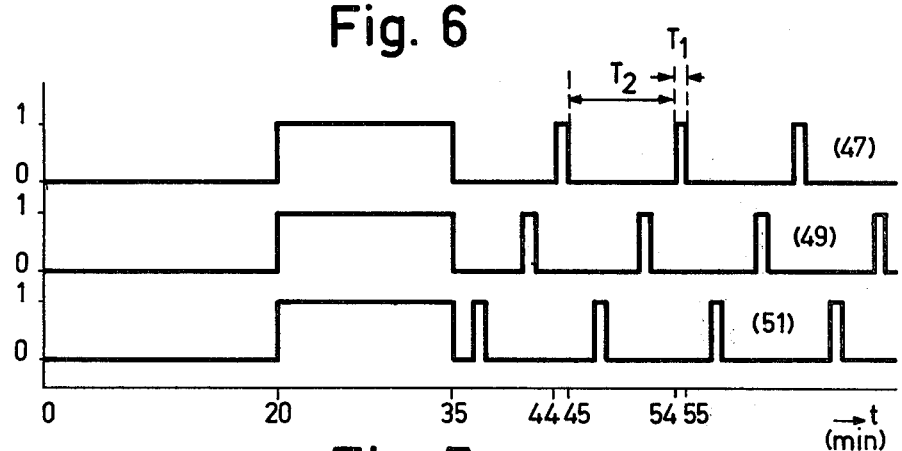
Figure 8:
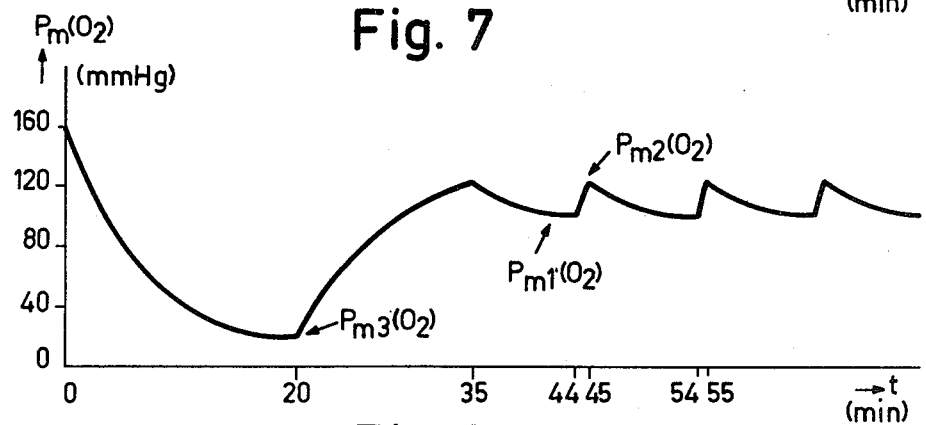

FIG. 1 is a diagrammatic sectional view of the skin on which a measuring head for measuring the partial oxygen pressure is arranged, FIG. 2 diagrammatically illustrated the equilibrium between the oxidation degree of haemoglobine and the partial oxygen pressure, FIG. 3 shows a diagram to illustrate the variation of the partial oxygen pressure between an artery and a measuring head, FIG. 4 is a cross-sectional view of an embodiment of a measuring head for a device in accordance with the invention, FIG. 5 is a bottom view of the measuring head shown in FIG. 4, FIG. 6 is a block diagram of an embodiment of a device in accordance with the invention, FIG. 7 shows a diagram illustrating the operation of the device shown in FIG. 6, and FIG. 8 shows a measuring curve.

In order to illustrate the problems occurring during the transcutaneous measurement of the arterial oxygen pressure, FIG. 1 symbollicly shows the situation of a measuring head 1 which is arranged on the skin and which is connected to a measuring and power supply circuit (not shown in FIG. 1), via a cable 3. Oxygen-rich blood of which the partial oxygen pressure is to be measured is applied to a bed of peripheral vessels 7 in which oxygen is given off to the surrounding tissue 9 via an artery 5. The blood is subsequently discharged via a vein 11. The oxygen given off to the tissue 9 diffuses via a layer of living cells 13 to a layer of dead cells 15 and finally reaches the measuring head 1.

Because oxygen is given off to the tissue 9 in the peripheral vessels 7, the partial oxygen pressure in these vessels is generally lower than that in the artery 5. However, it can be ensured that the peripheral vessels 7 are also filled with arterial blood by heating the tissue 7, with the result that the peripheral vessels widen to such an extent that the drop of the partial oxygen pressure in the blood becomes negligibly small thanks to the fast circulation. However, another effect occurs which will be explained with reference to FIG. 2.

In the blood an equilibrium exists between the partial oxygen pressure P(O$_2$), the concentration of oxidized haemoglobine C (HbO) and the concentration of deoxidized haemoglobine C (Hb). The percentage of oxidized haemoglobine is referred to as the saturation S(O$_2$):

$$S(O_2) = \frac{C(HbO)}{C(HbO) + C(Hb)} \times 100.$$

The relationship between S(O$_2$) and P(O$_2$) is shown in FIG. 2 at temperatures of 37° C. (uninterrupted curve) and 42° C. (stroke/dot curve). For normal venous blood, the equilibrium is situated approximately at the point which is indicated by the reference V, and for normal arterial blood approximately at the point indicated by the reference A. The Figure clearly shows that, the saturation remaining the same, the partial oxygen pressure increases by an amount $\Delta P_1$ when the blood is heated. As a result, the partial oxygen pressure in the tissue 9 is higher than if the peripheral vessels 7 were filled with arterial blood at a temperature of 37° C. The path from the artery 5 to the measuring head 1 is plotted horizontally in FIG. 3 (not to scale) and the oxygen pressure is vertically plotted. The arterial oxygen pressure Pa(O$_2$) is increased in the described manner, due to the heating of the blood in the peripheral vessels, by an amount $\Delta P_1$. In the dermis 13 oxygen is consumed by the living cells, thus causing a reduction of the oxygen pressure by an amount $\Delta P_2$.

The oxygen pressure at the area of the epidermis 15, therefore, is $P_a(O_2)+\Delta P_1-\Delta P_2$. This is the pressure $P_{mi}(O_2)$ which would be measured by means of an ideal measuring head. An ideal measuring head is a measuring head which does not consume oxygen itself and which is arranged on the skin in a completely leak-free manner, so that no oxygen can penetrate from the air. It is also assumed that no lateral leakage through the skin occurs. If oxygen enters from the air, the pressure $P_{mi}$(O$_2$) is further increased by an amount $\Delta P_{ml}$ and, if the measuring head consumes oxygen, this pressure is reduced again by an amount $\Delta P_{mc}$, so that the total oxygen pressure measured equals:

$$P_m(O_2)=P_a(O_2)+\Delta P_1-\Delta P_2+\Delta P_{ml}-\Delta P_{mc} \qquad (1)$$

The use of known devices for the transcutaneous measurement of Pa(O$_2$) is based on:

$$\Delta P_1-\Delta P_2+\Delta P_{ml}-\Delta P_{mc}=0 \qquad (2)$$

This assumption can be verified by measuring P$_a$(O$_2$) in a different manner, for example, by taking a blood sample. It has been found in practice that the relation (2) is satisfied reasonably well in many cases at a skin temperature of 44° C. However, certainty never exists in this respect and, moreover, a temperature of 44° C. leads to skin irritation after some time.

In order to avoid these drawbacks, the device in accordance with the invention comprises a measuring head 1 as shown in the FIGS. 4 and 5. This head comprises a metal housing 17 in which a body 19 of thermally insulating material is accommodated, said body comprising three measuring cells 21. The measuring cells 21 are known Clark cell comprising a heating element, for example, as described in said Netherlands Patent Specification No. 152,084 or in the article "Transcutaneous measurement of blood PO$_2$" by Renate Huch e.a. in J. Perinat. Med. 1 (1973), pages 183-191.

The surface 23 of the housing 17 which is to be arranged against the skin is preferably provided with an adhesive layer, so that intimate contact with the skin is obtained and only little oxygen leakage occurs. In order to minimize the oxygen entering, for example, through the skin, an annular measuring cell 25 of the Clark type is accommodated in the housing, the surface thereof which is to be arranged against the housing being situated in the same plane as a surface of the body 19 and the (heated) surface of the measuring cells 21 which is to be arranged against the skin. The annular measuring cell 25 is not provided with a heating element. It consumes a substantial part of the oxygen entering by leakage.

The measuring cells and heating elements are connected, via connection wires (not shown) and the cable 3, to a measuring and power supply circuit, the block diagram of which is shown in FIG. 6. Each of the measuring cells 21, 25 comprises an anode 27 which is made, for example, of Ag/AgCl, and a cathode 29 which is made of, for example, Pt. These electrodes are situated in a space filled with an electrolyte, for example, a solution of KCl. This space is separated from the surroundings by a diaphragm 31 which is permeable to O$_2$ and which is made of, for example, polytetrafluoroethylene. The electrodes 27, 29 are included, together with a voltage source 33, in a circuit in which an electrical current flows which is dependent on the partial oxygen pressure at the area of the diaphragm 31. In the measuring cells 21 which serve for the actual measurement this current is measured by means of a measuring resistor 35 across which a voltage arises which is proportional to this current and which is applied to the inputs of an amplifier 37. The outputs of the three amplifiers 37 are connected to the inputs of a recording measuring instrument 39.

As has already been stated, each of the three measuring cells 21 is provided with a heating element 41, for example, a resistance winding. These heating elements are connected to a power supply circuit which is formed by a voltage source 43 and three switches 47, 49 and 51 which are controlled by a control member 45. When the switch 47 is closed, the first heating element 41 (the upper element in FIG. 6) is active; when the switch 49 is closed, the second heating element is active, and when the switch 51 is closed, the third heating element is active. The switches 47, 49 and 51 may be, for example, relays or semiconductor switches. The control member 45 may comprise a mechanical or electronic clock which alternately opens and closes the three switches in accordance with the predetermined diagram. An example of such a diagram is shown in FIG. 7. Each of the three curves in this Figure represents the changing in the time of the state of one of the switches, the reference numeral whereby the switch is denoted in FIG. 6 being stated between brackets adjacent the relevant curve at the right. When a curve has the level denoted by "0", the relevant switch is open and if the curve has the level denoted by "1", the switch is closed.

It is assumed that the measuring head is arranged on the skin and the recording by means of the measuring instrument 39 commences at the instant t=0. One of the three curves produced by this measuring instrument is shown in FIG. 8. This curve represents the measuring result of the first measuring cell 21 (the upper cell in FIG. 6) as a function of the time.

FIG. 8 shows that the measuring cell indicates a partial oxygen pressure of 160 mm Hg at the instant t=0. This corresponds to the oxygen pressure in the ambient air, which is explained by the fact that a quantity of air is trapped between the measuring head and the skin when the measuring head is fitted.

As a result of the oxygen consumption of the measuring cells, the oxygen pressure $P_m(O_2)$ gradually drops to a constant value $P_{m3}(O_2)$ which is lower than the value normally found for venous blood. The latter value amounts to approximately 40 mm Hg, as appears from FIG. 2, and this approximately the value which could be expected if the skin were not heated. The difference is caused by the oxygen consumption in the dermis ($\Delta P_2$) and of the measuring cell ($\Delta P_{mc}$), reduced by the oxygen pressure increase due to ingress of air ($\Delta P_1$), in as far as this increase is not cancelled by the annular measuring cell 25. Therefrom, it follows that the following formula is a good approximation:

$$\Delta P_2 + \Delta P_{mc} - \Delta P_1 = 40 - P_{m3}(O_2) \qquad (3)$$

As appears from FIG. 7, all switches 47, 49, 51 are closed after 20 minutes. Subsequently, the skin is heated at the area of the three measuring cells 21 during 15 minutes. During this period, the partial oxygen pressure measured increases due to the widening of the peripheral vessels 7, which are thus filled with arterial blood, as well as by the shifting of the saturation curve (see FIG. 2).

At the instant t=35 minutes, all switches are opened again, after which they are periodically opened and closed, so that each heating element is each time actuated for $T_1$ minutes, with an interval of $T_2$ minutes between two successive actuation periods. The actuation of each of the heating elements starts $(T_1+T_2)/n$ minutes after the actuation of the preceding heating element, n being the number of heating elements. In the described example, n=3, $T_1$=1 minute and $T_2$=9 minutes.

The variation of the partial oxygen pressure measured per measuring cell during each heating and cooling period can be established on the basis of FIG. 8. After the opening of the switch 47, $P_m(O_2)$ gradually decreases to a substantially constant value $P_{m1}(O_2)$, thanks to the fact that the peripheral vessels 7 are comparatively quickly filled with fresh venous blood of normal temperature. Because the surrounding tissue 9 maintains its high temperature for a prolonged period of time, the widening of the peripheral vessels continues to exist.

When the heating is switched on again (t=44 minutes) the blood in the peripheral vessels is also heated again, so that the saturation curve is shifted and a higher partial oxygen pressure $P_{m2}(O_2)$ is measured. From this it follows that the following is a good approximation:

$$\Delta P_1 = P_{m2}(O_2) - P_{m1}(O_2) \qquad (4)$$

$\Delta P_1$ thus forms an indication for the temperature increases at the area of the peripheral blood vessels. The equation (1) was derived for heated blood, so that the value for $P_m(O_2)$ to be inserted therein equals $P_{m2}(O_2)$. The following equation is found by combination of the equations (1), (3) and (4):

$$P_d(O_2) = P_{m1}(O_2) + 40 - P_{m3}(O_2) \qquad (5)$$

FIG. 8 shows that the value $P_{m1}(O_2)$ is available for approximately 4 minutes per measuring cell 21. As a result of the phase shifted periodic actuation of the three heating elements 41, it is thus ensured that always at least one of the three measuring cells indicates the value $P_{m1}(O_2)$, so that the partial oxygen pressure of the blood is continuously measured. Because each heating element is actuated for only one minute per 10 minutes, no skin irritation occurs.

Obviously, the number of measuring cells 21 with heating element 41 can be extended, if desired. Alternatively, the heating can be realised in a different manner, for example, by high frequency heating or by direct heating of the annular cathode 29 which is connected as an electrical resistor. If desired, the skin temperature can be measured and the current through the heating elements can be controlled. Alternatively, the circuit shown in FIG. 6 may also be adapted so that a small current flows through the heating elements also when these elements are not actuated, in order to compensate for heat losses of the measuring head.

What is claimed is:

1. An electrochemical device for transcutaneous electrochemical measurement of the partial pressure of oxygen in the blood of humans or animals comprising:
   n measuring cells, n being equal to or greater than three, each measuring cell including electrodes, a surface for contacting the skin, and heating element means for heating the surface;
   a plurality of measuring circuits, a separate measuring circuit being operatively connected to the electrodes of each cell; and
   power supply means for periodic, sequential actuation of the heating element means, each of said heating element means being actuated for a first period of $T_1$ minutes which is followed by a second period of $T_2$ minutes during which the heating element means is not actuated, the heating element means being actuated in a sequence so that actuation of each heating element means commences at an instant $(T_1+T_2)/n$ minutes after the beginning of the actuation of the preceeding heating element means in the sequence.

2. A device as claimed in claim 1 further comprising:
   a measuring head which contains the measuring cells;
   a body having low heat conductivity which is mounted within the head and which includes means for mounting the measuring cells;
   an additional annular measuring cell which surrounds the n measuring cells and which includes a nonheated surface;
   the surfaces of the n measuring cells and of the additional measuring cell being disposed in a plane which is substantially the same plane as a surface of the body.

* * * * *